United States Patent [19]

Steacy

[11] Patent Number: 4,528,412
[45] Date of Patent: Jul. 9, 1985

[54] DEHYDROCYCLODIMERIZATION PROCESS

[75] Inventor: Paul C. Steacy, Des Plaines, Ill.
[73] Assignee: UOP Inc., Des Plaines, Ill.
[21] Appl. No.: 659,794
[22] Filed: Oct. 11, 1984
[51] Int. Cl.[3] .......................... C07C 3/03; C07C 7/01
[52] U.S. Cl. .................. 585/415; 585/413; 585/423; 585/424; 585/450
[58] Field of Search ............. 585/415, 403, 413, 423, 585/424, 450, 478; 55/26, 27, 28

[56] References Cited

U.S. PATENT DOCUMENTS

| | | | |
|---|---|---|---|
| 2,038,834 | 4/1936 | Frey | 585/415 |
| 2,735,876 | 2/1956 | Hess et al. | 585/403 |
| 2,900,427 | 8/1959 | Viles | 585/403 |
| 2,992,283 | 7/1961 | Eng | 260/673 |
| 3,101,261 | 4/1963 | Skarstrom | 55/58 |
| 3,537,978 | 11/1970 | Borst, Jr. | 208/101 |
| 3,574,089 | 4/1971 | Forbes | 208/101 |
| 3,761,389 | 9/1973 | Rollmann | 208/64 |
| 3,843,740 | 10/1974 | Mitchell et al. | 260/673 |
| 4,180,689 | 12/1979 | Davies et al. | 585/407 |
| 4,329,532 | 5/1982 | Conn et al. | 585/407 |
| 4,347,394 | 8/1982 | Detz et al. | 585/419 |
| 4,356,014 | 10/1982 | Higgins | 62/28 |
| 4,381,417 | 4/1983 | Vora et al. | 585/655 |
| 4,381,418 | 4/1983 | Gewartowski et al. | 585/655 |
| 4,444,988 | 4/1984 | Capsuto et al. | 585/415 |
| 4,456,779 | 6/1984 | Owen et al. | 585/424 |

Primary Examiner—D. E. Gantz
Assistant Examiner—A. Pal
Attorney, Agent, or Firm—Thomas K. McBride; John F. Spears, Jr.; William H. Page, II

[57] ABSTRACT

A hydrocarbon conversion process for the production of $C_6$–$C_8$ aromatic hydrocarbons from $C_3$ and $C_4$ aliphatic hydrocarbons is disclosed. This dehydrocyclodimerization process is characterized by the integrated product recovery steps employed to separate hydrogen and products from the reactor effluent. Following partial condensation of the reactor effluent stream, the resultant vapor is subjected to liquid absorption (scrubbing) followed by autorefrigeration to yield lighter gas streams. Liquids from the various steps are separated via fractionation.

18 Claims, 1 Drawing Figure

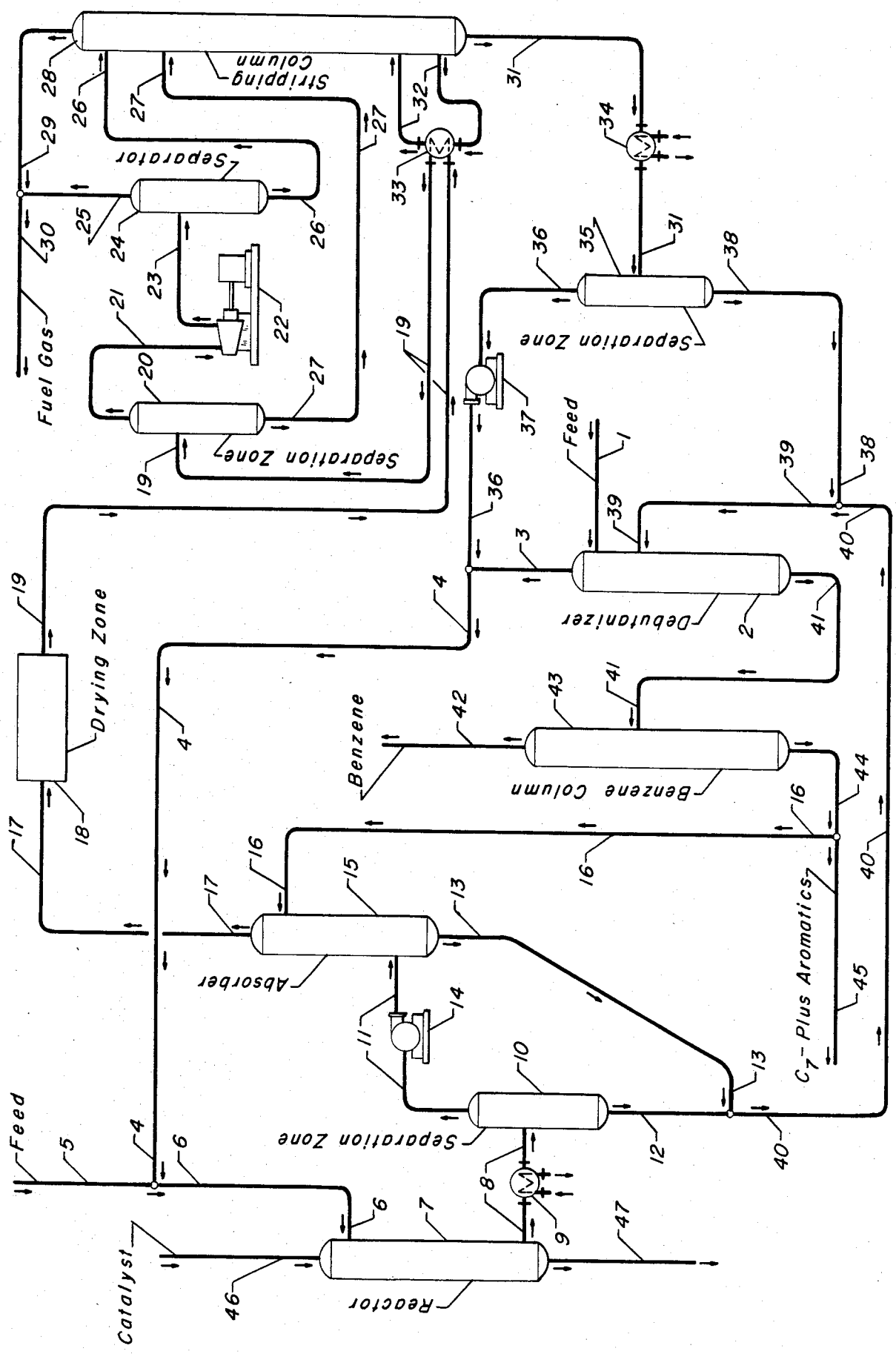

DEHYDROCYCLODIMERIZATION PROCESS

FIELD OF THE INVENTION

The subject process relates to a hydrocarbon conversion process. Specifically the subject process relates to a catalytic process referred to as dehydrocyclodimerization wherein two or more molecules of a light aliphatic hydrocarbon, such as propane, are joined together to form a product aromatic hydrocarbon. Nonaromatic hydrocarbons are also produced, especially when substantial amounts of olefins are present in the feed. The invention specifically relates to the separatory methods used to recover hydrogen and product aromatic hydrocarbons from a vapor phase reaction zone effluent stream. This separatory method also relates to techniques for recycling unconverted feed hydrocarbons to the reaction zone.

INFORMATION DISCLOSURE

There are a large number of references which describe the conversion of light alipahtic hydrocarbons to aromatic hydrocarbons. For instance, U.S. Pat. No. 2,992,283 issued to J. Eng describes the conversion of propylene to a variety of higher molecular weight hydrocarbons using a treated crystalline aluminosilicate as the catalyst. U.S. Pat. No. 4,347,394 issued to C. M. Detz et al describes the conversion of $C_5+$ hydrocarbons to aromatics using a nonacidic zeolite supporting a platinum compound. U.S. Pat. No. 4,329,532 issued to P. J. Conn et al describes the conversion of $C_4$-minus olefins or mixtures of olefins and paraffins to aromatic hydrocarbons. The catalyst comprises a crystalline silicate having a specified composition, crystallite size range, and X-ray diffraction pattern.

U.S. Pat. No. 4,180,689 issued to E. E. Davies et al describes the conversion of $C_3$–$C_8$ aliphatic hydrocarbons to aromatic hydrocarbons in a process which employs a catalyst comprising gallium supported on an aluminosilicate. U.S. Pat. No. 3,761,389 issued to L. D. Rollman et al describes an improved process for converting $C_2$ to 400° F. hydrocarbons to aromatics over a ZSM-5 type catalyst. The improvement resides in the use of two reaction stages in series, with the first being at more severe operating conditions. U.S. Pat. No. 3,843,740 issued to T. O. Mitchell et al also describes a process for aromatizing aliphatic feedstocks using two different catalysts in the reactor. This reference is also pertinent for the process diagram illustrating the recovery of the product aromatics by fractionation. U.S. Pat. No. 4,444,988 issued to L. M. Capsuto et al is pertinent for its showing of the product recovery steps employed in the conversion of a $C_2$–$C_5$ olefin into gasoline over a zeolitic catalyst.

The separation of product hydrocarbons from a reaction zone effluent stream which also contains light hydrocarbons and possibly hydrogen is important to the successful operation of several hydrocarbon conversion processes. For instance, U.S. Pat. Nos. 3,537,978 issued to W. B. Borst, Jr. and 3,574,089 issued to J. T. Forbes describe the recovery of naphtha, hydrogen-rich recycle gas, and light hydrocarbon streams from the effluent of a catalytic reforming zone. U.S. Pat. No. 3,101,261 issued to C. W. Skarstrom illustrates a process to recover hydrogen light ends and naphtha from the effluent of a reforming reaction zone. These references are pertinent for their showing of the use of such separatory techniques as partial condensation, stripping columns, and absorption.

U.S. Pat. No. 4,356,014 issued to R. D. Higgins is pertinent for the showing in FIGS. 1 and 3 of the utilization of expansion-compression trains, partial condensation and fractionation in a separation process. In FIG. 3 a stream in line 84 is separated and the resultant gas stream is depressurized in expander 24. This produces some liquid which is passed via line 88 into the fractionation column 29 together with liquid from the initial separation in vessel 86. U.S. Pat. Nos. 4,381,417 issued to B. V. Vora et al and 4,381,418 issued to S. A. Gewartowski et al describe product recovery systems for dehydrogenation processes. Referring to the latter reference, the reactor effluent is cooled, dried, further cooled, and then passed into a vapor-liquid separation zone 28. The vapors from this zone are depressurized in turbine 32 to yield a cold mixed phase stream collected in separation zone 34. Liquid from this zone is flashed into the separation zone 51.

SUMMARY OF THE INVENTION

The invention is a unique method of separating the product hydrogen and $C_6$-plus hydrocarbons from the vapor phase effluent stream of a dehydrocyclodimerization process. The process is characterized by a flow scheme which integrates absorptive scrubbing, autorefrigeration and fractionation in a highly energy-efficient manner. The process may be more specifically characterized as comprising the steps of passing a charge stream which comprises a $C_3$ or $C_4$ feed paraffin or olefin into a reaction zone and producing a vapor phase reaction zone effluent stream which comprises the unconverted feed hydrocarbon, hydrogen, by-product $C_1$ and $C_2$ hydrocarbons, benzene, toluene, and $C_8$ aromatic hydrocarbons or other $C_6$–$C_8$ product hydrocarbons partially condensing the reaction zone effluent stream, and in a first vapor-liquid separation zone separating the resultant admixture into a first vapor stream which comprises hydrogen, $C_1$ and $C_2$ hydrocarbons, the feed hydrocarbon and benzene and a first liquid stream which comprises benzene, toluene, and $C_8$ aromatic hydrocarbons; passing the first vapor stream through an absorption zone in which the first vapor stream is contacted with a lean absorption liquid stream and producing a second vapor stream which comprises hydrogen, $C_1$ and $C_2$ hydrocarbons, and the feed hydrocarbon and a rich absorption liquid stream which comprises the feed hydrocarbon, benzene, and toluene; partially condensing the second vapor stream, and in a second vapor-liquid separation zone separating the resultant admixture into a third vapor stream comprising hydrogen, $C_1$ and $C_2$ hydrocarbons and the feed hydrocarbon and a second liquid stream which comprises the feed hydrocarbon; depressurizing the third vapor stream under conditions which result in a partial condensation of the third vapor stream and the production of a fourth vapor stream which comprises hydrogen and $C_1$ hydrocarbons and a third liquid stream which comprises $C_2$ hydrocarbons and the feed hydrocarbon; passing the second and the third liquid streams into a stripping column operated at conditions effective to separate the entering hydrocarbons into a net overhead stream which comprises $C_1$ hydrocarbons and a net bottoms stream which comprises the feed hydrocarbon; recycling at least a portion of the net bottoms stream to the reaction zone as a portion of said feed stream; passing the first liquid stream and the rich absorption liquid stream into a fractionation zone operated at fractionation conditions which separate entering hydrocarbons into at least a $C_6$ hydrocarbon-rich process stream, a $C_7$-plus hydrocarbon-rich process stream, and a fifth vapor stream which comprises the feed hydrocarbon; and removing the benzene-rich process stream and a first portion of the $C_7$-plus hydrocarbon-rich process stream from the process as products and passing a second portion of the $C_7$-plus hydrocarbon-rich process stream into the absorption zone as the lean absorption liquid stream.

BRIEF DESCRIPTION OF THE DRAWING

The drawing is a simplified schematic diagram of a process which converts a propane-containing mixture fed through lines 1 and 5 into benzene removed in line 42 and $C_7$-plus aromatics removed in line 45. The effluent stream of the reactor 7 is partially condensed and separated into vapor and liquid phases. The vapor phase is processed through the absorber 15 and an autorefrigeration loop including expander 22. The liquid phase portion is transported into a fractionation zone comprising columns 2 and 43.

DETAILED DESCRIPTION

Processes for the conversion of light aliphatic hydrocarbons to aromatic or nonaromatic $C_6$-plus hydrocarbons have been the subject of significant development efforts as evidenced by the previously cited references. The basic utility of the process is the conversion of the low cost highly available $C_3$ and $C_4$ hydrocarbons into the more valuable aromatic hydrocarbons and hydrogen or to convert the feed hydrocarbons to higher molecular weight products. This may be desired simply to upgrade the value of the hydrocarbons. It may also be desired to correct an overabundance of the $C_3$ and $C_4$ hydrocarbons or to fulfill a need for the aromatic hydrocarbons. The aromatic hydrocarbons are highly useful in the production of a wide range of petrochemicals, with benzene being one of the most widely used basic feed hydrocarbon chemicals. The product aromatic hydrocarbons are also useful as blending components in high octane number motor fuels.

The feed compounds to the subject process are light aliphatic hydrocarbons having from 2 to 4 carbon atoms per molecule. The feed stream may comprise a single compound or a mixture of two or more of the compounds. The preferred feed compounds are propane, propylene, the butanes, and the butylenes, with saturates being highly preferred. The feed stream to the process may also contain some $C_2$ and $C_5$ hydrocarbons. However, it is greatly preferred that the concentration of $C_5$ hydrocarbons in the feed stream to the process is held to the minimum practical level. The preferred products of the process are $C_6$-plus aromatic hydrocarbons. Dehydrocyclodimerization processes are not 100% selective and some nonaromatic $C_6$-plus hydrocarbons are produced from saturate feeds. However, the very great majority of the $C_6$-plus product hydrocarbons will be benzene, toluene, and the various xylene isomers when processing a paraffinic feed. A small amount of $C_9$-plus aromatics is also produced. The presence of olefins in the feed stream results in the production of $C_6$-plus long chain hydrocarbons as products with the preferred catalyst system. Sizable olefin concentrations in the feed significantly decrease the production of aromatics.

The subject invention is directed to the recovery of the product hydrocarbons from the effluent stream of the reaction zone. Therefore, the configuration of the reaction zone and the composition of the catalyst employed within the reaction zone are not basic elements of the invention or limiting characteristics of the invention. Nevertheless, in order to provide a background to the subject invention, it is felt useful to describe the preferred reactor system. This system comprises a moving bed radial flow multi-stage reactor such as is described in U.S. Pat. Nos. 3,652,231; 3,692,496; 3,706,536; 3,785,963; 3,825,116; 3,839,196; 3,839,197; 3,854,887; 3,856,662; 3,918,930; 3,981,824; 4,094,814; 4,110,081 and 4,403,909. These patents also describe catalyst regeneration systems and various aspects of moving catalyst bed operations and equipment. This reactor system has been widely employed commercially for the reforming of naphtha fractions. Its use has also been described for the dehydrogenation of light paraffins.

This reactor system normally employs a spherical catalyst having a diameter between about 1/64 and $\frac{1}{8}$ inch. The catalyst preferably comprises a support material and a metallic component deposited on the support material as through impregnation or coprecipitation. The previously cited references point out that the current trend is the use of a zeolitic support material, with the catalyst referred to in the art as a ZSM-5 type zeolite being often specified as a preferred material. When properly formulated, it appears this zeolitic material by itself has significant activity for the dehydrocyclodimerization reaction. However, it is still preferred to employ a metallic component within the catalyst system to increase the activity of the catalyst. The preferred metallic component is gallium as described in the previously cited U.S. Pat. No. 4,180,689. A dehydrocyclodimerization reaction zone is preferably operated at a temperature between about 920°–1050° F. (487°–565° C.) and a pressure under 1000 psig. Hydrogen producing reactions are normally favored by lower pressures, and pressures under about 70 psig at the outlet of the reaction zone are highly preferred. Other conditions may be preferred for other reactions.

The drawing illustrates the preferred embodiment of the invention. Those skilled in the art will recognize that this process flow diagram has been simplified by the elimination of many necessary pieces of process equipment including some heat exchangers, process control systems, pumps, fractionation column overhead and reboiler systems, etc. It may also be readily discerned that the process flow presented in the drawing may be modified in many aspects without departing from the basic overall concept of the invention. For example, the heat exchange shown in the drawing has been held to a minimum for purposes of simplicity. Those skilled in the art will recognize that the choice of heat exchange methods employed to obtain the necessary heating and cooling at various points within the process is subject to a large amount of variation as to how it is performed. In a process as complex as this, there exists many possibilities for indirect heat exchange between different process streams. Depending on the specific location and circumstance of the installation of the subject process, it may also be desired to employ heat exchange against steam, hot oil, or process streams from other processing units not shown on the drawing.

Referring now to the drawing, the liquid feed stream may be split into two separate streams, one of which enters the process through line 1. The second and normally larger feed stream enters the process through line 5. For purposes of illustration, it is assumed in this instance that the feed stream is a mixture of hydrocarbons which is rich in propane and contains some isobutane and normal butane. The portion of the feed stream which enters through line 1 is fed to the top of a debutanizer column 2. The hydrocarbons which enter the debutanizer 2 are separated into a net bottoms stream removed through line 41 and a net overhead vapor stream removed through line 3. The overhead vapor stream of line 3, which is also referred to herein as a fifth vapor stream, is admixed with a vapor stream from line 36 and passed into line 4. The other portion of the feed stream from line 5 is admixed into the hydrocarbons flowing through line 4 to form a reactor charge stream carried by line 6. This charge stream will contain a mixture of propane, isobutane, and normal butane. The reactor charge stream will normally not contain significant amounts of hydrogen.

Freshly regenerated catalyst from line 46 enters the top of the reaction zone 7 and proceeds downward within an annular catalyst retaining volume. Used catalyst is withdrawn from the bottom of the reaction zone through line 47 and transferred to the appropriate catalyst regeneration facilities. The charge stream to the reaction zone enters through line 6 and preferably makes several passes through different sections of the catalyst bed, with interstage heating not shown being provided to supply the necessary heat for the endothermic dehydrocyclodimerization reaction. A highly olefinic charge stream would instead result in an endothermic reaction and interstage coolers would be required. This produces a vaporous reaction zone effluent stream carried by line 8 which contains aromatic hydrocarbons, $C_1$ and $C_2$ reaction by-products, and hydrogen in addition to the unconverted propane and butanes. The reaction zone effluent stream carried by line 8 is partially condensed by passage through indirect heat exchange means 9. The resultant admixture of vapor and liquid is passed into the first vapor-liquid separation zone 10 and is therein separated into a vapor phase stream removed through line 11 and a liquid phase stream removed through line 12.

The vapor phase stream of line 11 contains hydrogen, $C_1$ and $C_2$ by-products, propane, butanes and benzene. This vapor stream is compressed in means 14 and passed into a lower portion of the absorber 15. Preferably the vapor stream is compressed from a pressure less than 65 psig to a pressure above 300 psig. More preferably the vapor stream is compressed to a pressure between 350 and 850 psig, with pressures above 450 psig being highly preferred. The compressed vapors pass upward countercurrent to a descending stream of absorption liquid which enters the absorption column through line 16. Substantially all of the benzene present in the entering vapor stream is removed and becomes a part of the liquid phase stream traveling through the absorber. This produces a second vapor stream removed through line 17 which comprises hydrogen, $C_1$ to $C_4$ hydrocarbons, and toluene. This vapor phase stream is passed via line 17 into a drying zone 18. The drying zone removes water which might otherwise freeze in the downstream low temperature processing equipment. The thus-dried second vapor stream is transported through line 19 to an indirect heat exchange means 33 which is employed as a reboiler on the stripping column 28. Additional cooling is provided by means not shown. The second vapor stream is thereby cooled and partially condensed prior to passage into the second vapor-liquid separation zone 20. The vaporous material entering separation zone 20 is separated into a third vapor stream carried by line 21 and a second liquid stream carried by line 27. The vapor stream is depressured in the power recovery turbine 22 which delivers useful mechanical energy to a load such as an electrical generator. The depressured and lower temperature effluent of the turbine is passed through line 23 into a third vapor-liquid separator 24.

The second liquid stream removed from the separation zone 20 is passed into the stripping column 28, via line 27. Likewise a third liquid stream is removed from separator 24 via line 26 and passed into the stripping column. These liquid streams will contain the heavier hydrocarbons entering this autorefrigeration zone. The second liquid stream will therefore contain toluene and the feed propane and butanes. The third liquid stream of line 26 will contain propane. Both liquid streams will also contain dissolved lighter hydrocarbons and hydrogen. These lighter compounds are removed from the entering liquids in the stripping column 28 to form a net overhead vapor stream removed via line 29. This net overhead vapor stream will contain the hydrogen and $C_1$ and $C_2$ hydrocarbons. It is admixed with the fourth vapor stream of line 25, which comprises hydrogen and $C_1$ and $C_2$ hydrocarbons, to form a fuel gas stream removed from the process in line 30. The operation of the stripping column is adjusted to regulate the presence of $C_2$ hydrocarbons in the net bottoms stream as in some instances it may be desired to recycle $C_2$ hydrocarbons to the reaction zone. $C_4$ and $C_5$ hydrocarbons are not normally produced from a $C_3$ feed and will therefore be present in significant quantities only if contained in the feed stream.

The stripping column 28 is preferably reboiled by the heat supplied to a stream of bottoms liquid removed in line 32 for passage through the indirect heat exchange means 33. The remainder of the bottoms liquid is removed through line 31 as a net bottoms stream which is heated in the indirect heat exchange means 34. This stream is then passed into a fourth vapor-liquid separation zone 35 under conditions which affect the vaporization of a significant amount of propane and any $C_2$ hydrocarbons. This vaporized material is removed from the separation zone in line 36, compressed in means 37 and then recycled to the reaction zone via line 4. The liquid phase material collected in the fourth separation zone comprises propane, butane, and toluene and is removed in line 38.

A stream of rich absorption liquid containing benzene picked up in the absorber 15 is withdrawn through line 13 and admixed with the first liquid stream carried by line 12. The admixture of these two streams together with the fifth liquid stream carried by line 38 is passed into the first fractionation column 2 through lines 39 and 40. The heavier $C_6$-plus hydrocarbons which enter the fractionator 2 are concentrated into a net bottoms liquid stream passed into the second fractionation column 43 through line 41. $C_5$ hydrocarbons are thereby recycled to the reaction zone allowing the direct production of high purity $C_6$ hydrocarbons. The hydrocarbons charged to the second fractionation column are separated therein into a net overhead vapor stream removed through line 42 which preferably is a high purity benzene stream, but which also contains the relatively small amount of $C_5$ hydrocarbons produced by the process and entering this column. $C_5$ hydrocarbons which flow through line 3 are converted to heavier products. Toluene, xylenes, and heavier aromatic hydrocarbons are removed through line 44. The $C_7$-plus aromatic hydrocarbons are divided into a product stream removed through line 45 and a recycle stream carried by line 16 and passed into the absorber as the lean absorption liquid stream.

A preferred embodiment of the invention may accordingly be characterized as a dehydrocyclodimerization process which comprises the steps of: (a) passing a first feed stream which comprises a $C_3$–$C_4$ feed hydrocarbon into a first fractionation column which is operated at conditions which effect the separation of hydrocarbons which enter the first fractionation column into a first net overhead stream which comprises the feed hydrocarbon and is substantially free of $C_6$-plus hydrocarbons and a first net bottoms stream which comprises $C_6$–$C_8$ aromatic hydrocarbons; (b) passing the first net overhead stream through a dehydrocyclodimerization reaction zone maintained at dehydrocyclodimerization conditions which include the presence of a solid catalyst and thereby producing a vapor phase reaction zone effluent stream which comprises unconverted feed hydrocarbon, hydrogen, by-product $C_1$ and $C_2$ hydrocarbons, benzene, toluene and $C_8$ aromatic hydrocarbons; (c) partially condensing the reaction zone effluent stream, and in a first vapor-liquid separation zone separating the reaction zone effluent stream into a first vapor stream which comprises hydrogen, $C_1$ and $C_2$ hydrocarbons, the feed hydrocarbon, and benzene and a first liquid stream which comprises the feed hydrocarbon, benzene, toluene, and $C_8$ aromatic hydrocarbons; (d) removing benzene from the first vapor stream by passing the first vapor stream through an absorption zone maintained at benzene absorption-promoting conditions and wherein the first vapor stream is contacted with a lean absorption liquid stream and thereby producing a second vapor stream which comprises hydrogen, $C_1$ and $C_2$ hydrocarbons, the feed hydrocarbon, and a toluene and a rich absorption liquid stream which comprises the feed hydrocarbon, benzene, and toluene; (e) partially condensing the second vapor stream, and in a second vapor-liquid separation zone separating the resultant biphase admixture into a third vapor stream comprising hydrogen, $C_1$ and $C_2$ hydrocarbons, and the feed hydrocarbon and a second liquid stream which comprises the feed hydrocarbon and toluene; (f) depressurizing the third vapor stream in a power recovery means under conditions which result in a partial condensation of the third vapor stream and the production of a fourth vapor stream which comprises hydrogen and methane and a third liquid stream which comprises a $C_2$ hydrocarbon and the feed hydrocarbon; (g) passing the second and third liquid streams into a stripping column operated at conditions which effect the separation of hydrocarbons which enter the stripping column into a second net overhead stream which comprises $C_1$ hydrocarbons and a second net bottoms stream which comprises the feed hydrocarbon and toluene; (h) separating the second net bottoms stream in a third vapor-liquid separation zone maintained at conditions which promote the production of a fifth vapor stream which comprises the feed hydrocarbon and a fourth liquid stream which comprises toluene; (i) passing the fifth vapor stream into the reaction zone and passing the first liquid stream and the rich absorption liquid stream into the first fractionation column; (j) separating the first net bottoms stream in a second fractionation column into a third net overhead stream comprising benzene and a third net bottoms stream which comprises toluene and $C_8$ aromatic hydrocarbons and which is substantially free of benzene; and (k) withdrawing the third net overhead stream and a first portion of the third net bottoms stream as products, and passing a second portion of the third net bottoms stream into the absorption zone as the previously referred to lean absorption liquid.

The following example is presented to further illustrate the subject invention. This example is based on the projected operation of a commercial scale dehydrocyclodimerization unit employing a process flow similar to that shown in the drawing. These calculated results are believed to be highly accurate in their depiction of the actual operation of such a process. The actual flows will likely vary from this due to feed variations or different catalyst selectivities, etc. The feed stream to the process comprises a first stream having a total flow rate of approximately 1500 moles per hour. This stream comprises about 1040 moles per hour of propane and 460 moles per hour of isobutane and normal butane. This feed stream is fed directly into the reaction zone. A secondary feed stream of identical composition but having a flow rate of 200 moles per hour is passed into the top of the debutanizer column. The main feed stream together with the recycle stream is passed through the reactor to yield a reactor effluent stream having a total flow rate of about 3803 moles per hour. This stream contains about 670 moles per hour of propane, 45 moles per hour of butanes, 99 moles per hour of benzene, 175 moles per hour of toluene, 73 moles per hour of xylenes, and sizable quantities of hydrogen, methane, and ethane. The reactor effluent stream will also contain some ethylene, propylene, isobutylene, ethylbenzene, and $C_9$-plus aromatics. The reactor effluent stream is cooled to approximately 104° F. (40° C.) and passed into the first vapor-liquid separation zone or low pressure separator. This separator is operated at a pressure of approximately 65 psig. The reactor effluent stream enters the low pressure separator as a mixed phase stream which is separated into the first liquid stream having a flow rate of about 331 moles per hour and the first vapor stream having a flow rate of about 3471 moles per hour. At these conditions, the first vapor stream will contain over 95% of the $C_3$-minus hydrocarbons and hydrogen which enters the separation zone. The vapor stream will also contain heavier hydrocarbons including about 44 moles per hour of $C_4$ hydrocarbons, 35 moles per hour of benzene, and about 27 moles per hour of toluene.

The first vapor stream emanating from the low pressure separator is compressed in a two-stage compression train having a cooler and condensate separation drum system. There is thereby delivered to the bottom of the absorption column a gas stream having a temperature of about 70° F. (21° C.) and a pressure of about 514 psig. This gas stream travels upward through the absorption column countercurrent to a lean oil stream which enters the top of the column at a temperature of about 60° F. (15.6° C.) at a flow rate of approximately 36 moles per hour. This treatment of the gas stream removes substantially all of the benzene from the gas stream.

It also removes some propane, but releases toluene to the gas stream. The net gas stream leaving the absorber has a flow rate of about 3156 moles per hour. This gas stream is cooled from 85° F. (29.4° C.) to about 33° F. (0.6° C.) through indirect heat exchange in the stripping column reboiler. It is then further cooled by indirect heat exchange to a temperature of −12° F. (−24.4° C.)

and passed into the cold high pressure separator or second vapor-liquid separation zone at a pressure of approximately 477 psig. The liquid collected in the cold high pressure separator is removed at a flow rate of approximately 761 moles per hour. The vapor stream, referred to herein as the third vapor stream, removed from the cold high pressure separator has a flow rate of approximately 2395 moles per hour and is depressured to approximately 60 psig in an expansion turbine.

This reduces the temperature of the stream to approximately −105° F. (−76° C.). The effluent of the expander is passed into a vapor-liquid separator, and is therein separated into a third liquid stream having a flow rate of about 153 moles per hour and the fourth vapor stream which is discharged to the fuel gas system. This third liquid stream together with the liquid stream removed from the cold high pressure separator are passed into the stripping column at different elevations separated by at least two or more fractionation trays. The net fuel gas stream has a flow rate of approximately 2648 moles per hour. The overhead vapor stream removed from the light ends stripping column has a temperature of −36° F. (−38° C.) and a pressure of 60 psig. The stripping column is operated with a bottoms liquid temperature of approximately 1° F. (−17° C.) The stripper overhead stream contains about 135 moles per hour of methane, 175 moles per hour of ethane, and 69 moles per hour of propane. The net bottoms stream of the stripping column has a flow rate of approximately 508 moles per hour of which about 391 moles per hour are propane. The net stripping column bottoms stream also contains ethane, propylene, isobutane and normal butane, and toluene. The net bottoms stream is separated in a vapor-liquid separation zone operated at a temperature of approximately 10° F. (−12° C.) and a pressure of 30 psig. This produces a vapor stream having a flow rate of approximately 442 moles per hour which is recycled to the reaction zone and a liquid stream which is passed into the debutanizer column.

The debutanizer column overhead stream has a flow rate of approximately 543 moles per hour. This stream contains about 349 moles per hour of propane and 92 moles per hour of butane. It also contains significant quantities of ethane and methane and smaller quantities of hydrogen, ethylene, propylene, isobutylene, and benzene. The debutanizer overhead vapor stream has a temperature of about 96° F. (35.6° C.) and a pressure of 125 psig. The debutanizer is operated with a bottoms liquid temperature of approximately 415° F. (212° C.). The net debutanizer bottoms stream has a flow rate of about 506 moles per hour. This stream contains approximately 97 moles per hour benzene, 198 moles per hour toluene, and about 20 moles per hour of $C_9$-plus aromatics, with the remainder of this stream being $C_8$ aromatics. The benzene-rich overhead stream of the second fractionation column, also referred to herein as the benzene column, has a flow rate of approximately 98 moles per hour of high purity benzene. The remainder of the hydrocarbons entering the benzene column are divided into the lean absorption liquid stream and a net $C_7$-plus aromatic stream having a flow rate of about 272 moles per hour.

It is believed that those of ordinary skill in the art of petroleum and petrochemical process design may determine proper vessel designs, operating conditions and procedures for the subject process through the use of standard process design techniques after having now been appraised of the overall flow of the process. These design techniques include a recognition that it is undesirable to pass compounds which may tend to freeze or otherwise solidify in the low temperature portion of the process downstream of the expansion turbine. For this reason, the absorption zone is provided to remove benzene from the gas stream entering this section of the process. Likewise, a drying zone is preferably provided. The function of this drying zone is to prevent the passage of water into the low temperature equipment. The drying zone is basically required to remove the small amount of water which may be dissolved within the feed stream to the process and any water which may be present on regenerated catalyst passed into the process or released from stripping steam used to seal catalyst passageways, etc. The drying zone is preferably a swing bed desiccant-type system. It is preferred to use two beds of a suitable absorbent alumina, with facilities being provided to regenerate one of these beds while the other bed is onstream.

The vapor-liquid separation zones employed within the process preferably comprise a suitably sized vertically oriented vessel having a demisting pad or other liquid entrainment removal means provided at the upper end. The various fractionation columns employed in the process are preferably trayed fractionation columns having sieve-type trays and being of relatively standard design. For instance, a properly designed column having 15 trays will function as the stripping column, while the first or debutanizer column may contain 22 trays and the benzene or second column may contain 55 trays. The liquid employed as the lean absorption liquid is preferably a portion of the net bottoms stream of the second fractionation column. However, it is within the scope of the subject process that a sidecut stream removed from this or another column could be employed as the lean absorption liquid stream. Other variations in the arrangement of the fractionation columns are also possible. For instance, it is possible to replace the portion of the feed stream charged to the top of the debutanizer column with an overhead condensing system. The entire single feed stream would then flow directly into the reactor. Another process flow variation is the passage of the net bottoms stream removed from the stripping column directly into the debutanizer column without intermediate flash separation. The arrangement shown in the drawing is preferred but either system would result in the recycling of the propane and other light feed hydrocarbons to the reaction zone.

I claim as my invention:

1. A process for the production of $C_6$-plus hydrocarbons which comprises the steps of:
    (a) passing a reactor charge stream which comprises a $C_3$ or $C_4$ aliphatic feed hydrocarbon into a reaction zone maintained at dehydrocyclodimerization conditions which include the presence of a solid catalyst and producing a vapor phase reaction zone effluent stream which comprises unconverted feed hydrocarbon, hydrogen, by-product $C_1$ and $C_2$ hydrocarbons, benzene, toluene, and $C_8$ aromatic hydrocarbons;
    (b) partially condensing the reaction zone effluent stream, and in a first vapor-liquid separation zone separating the resultant admixture into a first vapor stream which comprises hydrogen, $C_1$ and $C_2$ hydrocarbons, the feed hydrocarbon and benzene and a first liquid stream which comprises benzene, toluene, and $C_8$ aromatic hydrocarbons;

(c) passing the first vapor stream through an absorption zone maintained at benzene absorption-promoting conditions and in which the first vapor stream is contacted with a lean absorption liquid stream and producing a second vapor stream which comprises hydrogen, $C_1$ and $C_2$ hydrocarbons, and the feed hydrocarbon and a rich absorption liquid stream which comprises the feed hydrocarbon, benzene, and toluene;

(d) partially condensing the second vapor stream, and in a second vapor-liquid separation zone separating the resultant admixture into a third vapor stream comprising hydrogen, $C_1$ and $C_2$ hydrocarbons and the feed hydrocarbon and a second liquid stream which comprises the feed hydrocarbon;

(e) depressurizing the third vapor stream under conditions which result in a partial condensation of the third vapor stream and the production of a fourth vapor stream which comprises hydrogen and $C_1$ hydrocarbons and a third liquid stream which comprises $C_2$ hydrocarbons and the feed paraffin;

(f) passing the second and the third liquid streams into a stripping column operated at conditions effective to separate the entering hydrocarbons into a net overhead stream which comprises $C_1$ hydrocarbons and a net bottoms stream which comprises the feed hydrocarbon;

(g) recycling at least a portion of the net bottoms stream to the reaction zone as a portion of said feed stream;

(h) passing the first liquid stream and the rich absorption liquid stream into a fractionation zone operated at fractionation conditions which separate entering hydrocarbons into at least a $C_6$ hydrocarbon-rich process stream, a $C_7$-plus hydrocarbon-rich process stream, and a fifth vapor stream which comprises the feed hydrocarbon; and (i) removing the $C_6$ hydrocarbon-rich process stream and a first portion of the $C_7$-plus hydrocarbon-rich process stream from the process as products and passing a second portion of the $C_7$-plus hydrocarbon-rich process stream into the absorption zone as the previously referred to lean absorption liquid stream.

2. The process of claim 1 further characterized in that the fractionation zone comprises a first and a second fractionation column with the first liquid stream and the rich absorption liquid stream being passed into the first fractionation column.

3. The process of claim 2 further characterized in that the net bottoms stream of the stripping column is flash separated into a sixth vapor stream which comprises the feed hydrocarbon and a fourth liquid stream which comprises benzene and the feed hydrocarbon, with the fourth liquid stream being passed into the first fractionation column.

4. The process of claim 3 further characterized in that a feed stream comprising the feed hydrocarbon is passed into the first fractionation column, and in that the fifth vapor stream is removed from the first fractionation column as a net overhead vapor stream and is passed into the reactor.

5. The process of claim 1 further characterized in that propane is a feed hydrocarbon.

6. The process of claim 5 further characterized in that propylene is a feed hydrocarbon.

7. The process of claim 1 further characterized in that a butane is a feed hydrocarbon.

8. The process of claim 7 further characterized in that a butylene is a feed hydrocarbon.

9. The process of claim 1 further characterized in that the solid catalyst comprises gallium and a zeolitic support material.

10. A dehydrocyclodimerization process which comprises the steps of:
(a) passing a first feed stream which comprises a $C_3$-$C_4$ feed hydrocarbon into a first fractionation column which is operated at conditions which effect the separation of hydrocarbons which enter the first fractionation column into a first net overhead stream which comprises the feed hydrocarbon and is substantially free of $C_6$-plus hydrocarbons and a first net bottoms stream which comprises $C_6$-$C_8$ aromatic hydrocarbons;

(b) passing said first net overhead stream through a dehydrocyclodimerization reaction zone maintained at dehydrocyclodimerization conditions which include the presence of a solid catalyst and thereby producing a vapor phase reaction zone effluent stream which comprises unconverted feed hydrocarbon, hydrogen, by-product $C_1$ and $C_2$ hydrocarbons, benzene, toluene, and $C_8$ aromatic hydrocarbons;

(c) partially condensing the reaction zone effluent stream, and in a first vapor-liquid separation zone separating the reaction zone effluent stream into a first vapor stream which comprises hydrogen, $C_1$ and $C_2$ hydrocarbons, the feed hydrocarbon, and benzene and a first liquid stream which comprises the feed hydrocarbon, benzene, toluene, and $C_8$ aromatic hydrocarbons;

(d) removing benzene from the first vapor stream by passing the first vapor stream through an absorption zone maintained at benzene absorption-promoting conditions and wherein the first vapor stream is contacted with a lean absorption liquid stream and thereby producing a second vapor stream which comprises hydrogen, $C_1$ and $C_2$ hydrocarbons, the feed hydrocarbon, and toluene and a rich absorption liquid stream which comprises the feed hydrocarbon, benzene, and toluene;

(e) partially condensing the second vapor stream, and in a second vapor-liquid separation zone separating the resultant biphase admixture into a third vapor stream comprising hydrogen, $C_1$ and $C_2$ hydrocarbons, and the feed hydrocarbon and a second liquid stream which comprises the feed hydrocarbon and toluene;

(f) depressurizing the third vapor stream in a power recovery means under conditions which result in a partial condensation of the third vapor stream and the production of a fourth vapor stream which comprises hydrogen and methane and a third liquid stream which comprises a $C_2$ hydrocarbon and the feed hydrocarbon;

(g) passing the second and the third liquid streams into a stripping column operated at conditions which effect the separation of hydrocarbons which enter the stripping column into a second net overhead stream which comprises $C_1$ hydrocarbons and a second net bottoms stream which comprises the feed hydrocarbon and toluene;

(h) separating the second net bottoms stream in a third vapor-liquid separation zone maintained at conditions which promote the production of a fifth vapor stream which comprises the feed hydrocarbon and a fourth liquid stream which comprises toluene;

(i) passing the fifth vapor stream into the reaction zone and passing the first liquid stream and the rich absorption liquid stream into the first fractionation column;

(j) separating the first net bottoms stream in a second fractionation column into a third net overhead stream comprising benzene and a third net bottoms stream which comprises toluene and $C_8$ aromatic hydrocarbons and which is substantially free of benzene; and (k) withdrawing the third net overhead stream and a first portion of the third net bottoms stream as products, and passing a second portion of the third net bottoms stream into the absorption zone as the previously referred to lean absorption liquid.

11. The process of claim 10 further characterized in that the second vapor stream is cooled by indirect heat exchange against liquid removed from the stripping column prior to passage into the second vapor-liquid separation zone.

12. The process of claim 10 further characterized in that the third liquid stream is passed into the stripping column at a higher elevation than the second liquid stream is passed into the stripping column.

13. The process of claim 10 further characterized in that a second feed stream is admixed into the first net overhead stream.

14. The process of claim 10 further characterized in that the feed hydrocarbon is propane.

15. The process of claim 14 further characterized in that the first feed stream comprises propylene.

16. The process of claim 10 further characterized in that the first feed stream comprises a butane.

17. The process of claim 16 further characterized in that the first feed stream comprises a butylene.

18. The process of claim 9 further characterized in that the solid catalyst comprises gallium and a zeolitic support.

* * * * *